(12) United States Patent
Dhalla et al.

(10) Patent No.: US 7,304,189 B2
(45) Date of Patent: Dec. 4, 2007

(54) METHODS FOR PREPARING 1,1,1-TRIS(4-HYDROXYPHENYL)ALKANES

(75) Inventors: Adil Minoo Dhalla, Mumbai (IN); Raina Gupta, Karnataka (IN); Gurram Kishan, Bangalore (IN); Yongcheng Li, Montgomery, AL (US); G. V. Ramanarayanan, Karnataka (IN)

(73) Assignee: General Electric Company, Schenectady, NY (US)

( * ) Notice: Subject to any disclaimer, the term of this patent is extended or adjusted under 35 U.S.C. 154(b) by 279 days.

(21) Appl. No.: 11/046,921

(22) Filed: Jan. 31, 2005

(65) Prior Publication Data

US 2006/0173222 A1 Aug. 3, 2006

(51) Int. Cl.
*C07C 39/12* (2006.01)
(52) U.S. Cl. .................. 568/720; 552/115
(58) Field of Classification Search ............ 558/70; 568/70, 720
See application file for complete search history.

(56) References Cited

U.S. PATENT DOCUMENTS

| | | | |
|---|---|---|---|
| 3,579,542 A | 5/1971 | Meyer et al. | |
| 4,992,598 A | 2/1991 | Strutz et al. | |
| 5,672,776 A | 9/1997 | McCloskey et al. | |
| 5,756,781 A | * 5/1998 | Sybert et al. | 552/115 |
| 5,756,859 A | 5/1998 | McCloskey et al. | |
| 5,763,686 A | * 6/1998 | McCloskey et al. | 568/720 |

FOREIGN PATENT DOCUMENTS

EP 0847975 A1 6/1998

* cited by examiner

*Primary Examiner*—Yvonnie Eyler
*Assistant Examiner*—Sudhakar Katakam

(57) ABSTRACT

A method for preparing 1,1,1,-tris(4-hydroxyphenyl)alkanes generally comprises reacting a mixture of an aromatic hydroxy compound and a ketone in the presence of at least one ion exchange resin catalyst and optionally a co-catalyst to produce the 1,1,1-tris(4-hydroxyphenyl)alkanes of formula:

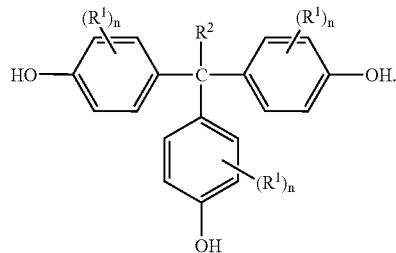

19 Claims, No Drawings

METHODS FOR PREPARING 1,1,1-TRIS(4-HYDROXYPHENYL)ALKANES

BACKGROUND

The present disclosure generally relates to a method for preparing 1,1,1-tris(4-hydroxyphenyl)alkanes.

The 1,1,1-tris(4-hydroxyphenyl)alkanes, such as, for example, those disclosed in U.S. Pat. Nos. 3,579,542 and 4,992,598, can be used as branching agents during the polymerization of polycarbonates. As such, it may be incorporated into reaction mixtures containing dihydroxy aromatic compounds such as bisphenol A and carbonate sources such as phosgene or diphenyl carbonate, among others.

An exemplary 1,1,1-tris(4-hydroxyphenyl)alkane, 1,1,1,-tris(4-hydroxphenyl)ethane (also referred to as THPE), can generally be prepared by the reaction of 4-hydroxyacetophenone with phenol. The reaction is analogous to the well known reaction of phenol with acetone to form 2,2-bis(4-hydroxyphenyl)propane (also commonly referred to as "bisphenol A"). U.S. Pat. No. 5,756,781 discloses reacting "phenol and 4-hydroyxacetophenone" in the presence of effective amounts of an ion exchange catalyst and a mercaptan as a co-promoter such that the resulting 1,1,1-tris(4'-hydroxyphenyl)ethane is substantially free of various reaction impurities.

U.S. Pat. No. 5,756,859 discloses reacting "phenol and 2,4-pentanedione under acidic conditions and in the presence of an effective amount of mercapto compound as promoter." This patent further states that "[t]he acidic conditions may be provided by the addition of any acidic material, especially a relatively volatile material such as hydrogen chloride." The patent next states that "[t]ypically, hydrogen chloride gas is passed through the mixture during the reaction."

Among the disadvantages to this method are that the quantity of catalyst used is relatively high and the volatile acids employed, e.g., hydrogen chloride gas, are generally corrosive. Other methods include the use of sulfuric acid in conjunction with 3-mercaptosulfonic acid as the promoter.

Accordingly, there remains a need in the art of efficient methods for preparing 1,1,1-tris(4-hydroxyphenyl)alkanes in high yields.

BRIEF SUMMARY

Disclosed herein is a method for producing 1,1,1-tris(4-hydroxyphenyl)alkanes. The method comprises reacting a mixture of an aromatic hydroxy compound and a ketone in the presence of at least one ion exchange resin catalyst and optionally a co-catalyst to produce the 1,1,1-tris(4-hydroxyphenyl)alkane.

In one embodiment is provided a method for producing 1,1,1-tris(4-hydroxyphenyl)ethane. The method comprises reacting a mixture of phenol and 2,4-pentanedione in the presence of at least one ion exchange resin catalyst and optionally a co-catalyst to form the 1,1,1-tris(4-hydroxyphenyl)ethane.

The above-described method may be understood more readily by reference to the following detailed description of the various features of the disclosure and the examples included therein.

DETAILED DESCRIPTION

The present disclosure may be understood more readily by reference to the following detailed description of preferred embodiments of the disclosure and the examples included therein. In the following specification and the claims that follow, reference will be made to a number of terms that shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

The modifier "about" used in connection with a quantity is inclusive of the stated value and has the meaning dictated by the context (e.g., includes the degree of error associated with measurement of the particular quantity).

As used herein the term "aliphatic radical" refers to a radical having a valence of at least one comprising a linear or branched array of atoms, wherein the array of atoms is not cyclic. The array may include heteroatoms such as nitrogen, oxygen, sulfur, silicon, and phosphorous, or may be composed exclusively of carbon and hydrogen. Examples of suitable aliphatic radicals include methyl, methylene, ethyl, ethylene, hexyl, n-propyl, isopropyl, n-butyl, sec-butyl, tertiary-butyl, pentyl, neopentyl, hexyl, heptyl, octyl, nonyl, decyl, undecyl, dodecyl, hexamethylene, trifluoromethyl, trifluoroethyl, methoxy, ethyloxy, oxyethyleneoxy ($O(CH_2)_2 O$), trimethylsilyl, mixtures thereof, and the like. The aliphatic radicals may be substituted or unsubstituted and may comprise one or more substituents including amino groups, halogen atoms, cyano groups, nitro groups, hydroxyl groups, mercapto groups, $C_1$-$C_{10}$ alkyl groups, $C_1$-$C_{10}$ alkoxy groups, $C_1$-$C_{10}$ alkoxycarbonyl groups, $C_1$-$C_{10}$ alkylthio groups, $C_1$-$C_{10}$ alkylamino groups, and the like.

As used herein the term "aromatic radical" refers to a radical having a valence of at least one comprising at least one aromatic group. Examples of aromatic radicals include phenyl, pyridyl, furanyl, thienyl, naphthyl, biphenyl, pyrrolyl, phenyl, biphenylene and mixtures thereof. The term includes groups containing both aromatic and aliphatic and or cycloaliphatic components, for example a benzyl group or an indanyl group. Aromatic radicals may be substituted or unsubstituted and may further comprise one or more heteroatoms including and/or substituents including amino groups, halogen atoms, cyano groups, nitro groups, hydroxyl groups, mercapto groups, $C_1$-$C_{10}$ alkyl groups, $C_1$-$C_{10}$ alkoxy groups, $C_1$-$C_{10}$ alkoxycarbonyl groups, $C_1$-$C_{10}$ alkylthio groups, $C_1$-$C_{10}$ alkylamino groups, mixtures thereof and the like.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may further comprise one or more non-cyclic components. For example, a cyclohexylmethyl group ($C_6H_{11}CH_2$—) is a cycloaliphatic radical that comprises a cyclohexyl ring (the array of atoms which is cyclic but which is not aromatic) and a methylene group (the non-cyclic component). The cycloaliphatic radical may comprise heteroatoms such as nitrogen, sulfur, selenium, silicon and oxygen, or may be composed exclusively of carbon and hydrogen. Cycloaliphatic radicals may be "substituted" or "unsubstituted". A substituted cycloaliphatic radical is defined as a cycloaliphatic radical, which comprises at least one substituent. A substituted cycloaliphatic radical may comprise as many substituents as there are positions available on the cycloaliphatic radical for substitution. Substituents which may be present on a cycloaliphatic radical include but are not limited to halogen atoms such as fluorine, chlorine, bromine, and iodine. Substituted cycloaliphatic radicals include trifluoromethylcyclohexyl, hexafluoroisopropylidenebis-(4-cyclohexyloxy) (i.e., —O $C_6H_{10}C(CF_3)_2$ $C_6H_{10}O$—), chloromethylcyclohexyl; 3-trifluorovinyl-2-cyclopropyl; 3-trichloromethylcyclohexyl (i.e., 3-$CCl_3C_6H_{10}$—), bromopropylcyclohexyl (i.e., $BrCH_2CH_2CH_2$ $C_6H_{10}$—), and the like. For convenience, the term "unsubstituted cycloaliphatic radical" is defined herein to encompass a wide range of functional groups. Examples of suitable cycloaliphatic radicals include cyclobutyl, cyclopentyl, cyclohexyl, methylcyclohexyl, cycloheptyl, 4-allyloxycyclohexyl, aminocyclohexyl (i.e., $H_2N$ $C_6H_{10}$—), aminocarbonylcyclopentyl (i.e., $NH_2COC_5H_8$—), 4-acetyloxycyclohexyl, dicyanoisopropylidenebis(4-cyclohexyloxy) (i.e., —O $C_6H_{10}C(CN)_2$ $C_6H_{10}O$—), 3-methylcyclohexyl, methylenebis(4-cyclohexyloxy) (i.e., —O $C_6H_{10}CH_2$ $C_6H_{10}O$—), ethylcyclobutyl, cyclopropylethenyl, 3-formyl-2-terahydrofuranyl, 2-hexyl-5-tetrahydrofuranyl; hexamethylene-1,6-bis(4-cyclohexyloxy) (i.e., —O $C6H_{10}$ $(CH_2)_6C_6H_{10}O$—); 4-hydroxymethylcyclohexyl (i.e., 4-$HOCH_2$ $C6H_{10}$—), 4-mercaptomethylcyclohexyl (i.e. 4-$HSCH_2$ $C_6H_{10}$—), 4-methylthiocyclohexyl (i.e., 4-$CH_3S$ $C_6H_{10}$—), 4-methoxycyclohexyl, 2-methoxycarbonylcyclohexyloxy (2-$CH_3OCO$ $C_6H_{10}O$ —), nitromethylcyclohexyl (i.e., $NO_2CH_2C_6H_{10}$—), trimethylsilylcyclohexyl, t-butyldimethylsilylcyclopentyl, 4-trimethoxysilylethylcyclohexyl (i.e.,. $(CH_3O)_3SiCH_2CH_2C_6H_{10}$—), vinylcyclohexenyl, vinylidenebis(cyclohexyl), and the like. The term "a $C_3$-$C_{10}$ cycloaliphatic radical" includes substituted cycloaliphatic radicals and unsubstituted cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

Disclosed herein are processes for preparing 1,1,1-tris(4-hydroxyphenyl)compounds such as those represented by Formula (I),

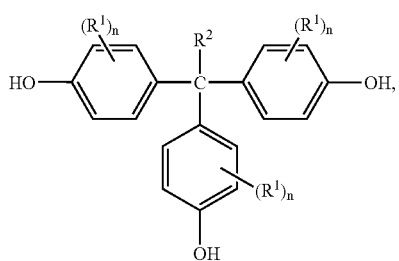

wherein $R^1$ and $R^2$ are independently at each occurrence selected from the group consisting of an aliphatic radical, an aromatic radical, and a cycloaliphatic radical, wherein "n" is an integer of value 0-3. Advantageously, these compounds can be used as branching agents in the preparation of polymers.

In accordance with the present disclosure, the process for preparing the 1,1,1-tris(4-hydroxyphenyl)compounds generally comprises reacting an aromatic hydroxy compound of Formula (II),

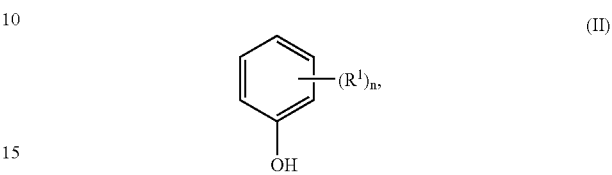

with a ketone of Formula (III);

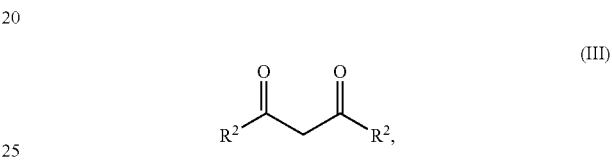

wherein $R^1$, $R^2$, and "n" have the same meaning as defined above. The aromatic hydroxy compound and the ketone are reacted in the presence of at least one ion exchange resin catalyst and optionally a co-catalyst.

In one embodiment, the aromatic hydroxy compound may be selected from the group consisting of substituted or unsubstituted phenols. Examples of suitable aromatic hydroxy compounds include, but are not limited to, 2,6-dimethylphenol, 2,3,6-trimethylphenol, 2,6-di-tert-butylphenol, 2-tert-butylphenol, meta-cresol, ortho-cresol, ortho-phenylphenol, ortho-benzylphenol, and mixtures of the foregoing aromatic hydroxy compounds. In one particular embodiment, the aromatic hydroxy compound is phenol.

Exemplary ketones of Formula (III) include, but are not intended to be limited to, 2,4-pentanedione. This particular ketone, while not intended to be limiting, can generally be utilized because of its commercial availability and low cost, among others. In one embodiment, the 1,1,1-tris(4-hydroxyphenyl)alkane prepared by the method of this disclosure is 1,1,1-tris(4-hydroxyphenyl)ethane (THPE).

The molar ratio of the aromatic hydroxy compound to the ketone is 3-30 to 1. In one embodiment, the molar ratio of the aromatic hydroxy compound to the ketone is 8-15 to 1. In other embodiments, the molar ratio of the aromatic hydroxy compound to ketone is 10-15 to 1.

The reaction of the aromatic hydroxy compound with the ketone can be achieved either in a batch mode or in a continuous mode. Typically, when the reaction is carried out in a batch mode the aromatic hydroxy compound, the ketone, the optional co-catalyst and the ion exchange resin catalyst are mixed and the reaction temperature is maintained at about 30° C. to about 120° C., and more specifically at about 40° C. to about 100° C. In one embodiment, the reaction temperature is at about 55° C. to about 75° C. The temperature of the reaction can be measured by using thermocouples inserted into the mixture or by measuring the temperature of the external heating media, for example, measuring the temperature of the oil bath. In one embodiment, the ketone is added drop-wise to a mixture of the aromatic hydroxy compound, the optional co-catalyst, and the ion exchange resin catalyst. The time taken for the reaction of the aromatic hydroxy compound and the ketone in a batch mode varies from about 5 hours to about 50 hours. In other embodiments, the reaction time varies from about 15 to about 40 hours and in still other embodiments, the reaction time varies from about 20 hours to about 30 hours.

In the continuous mode, a mixture of the aromatic hydroxy compound, the ketone, and the optional co-catalyst is passed through a reactor comprising a fixed bed of the ion exchange resin catalyst. The mixture is maintained at a temperature wherein the reactants remain in a liquid state. Typically, the mixture is maintained at a temperature of about 40° C. to about 65° C., and more specifically at a temperature of about 45° C. to about 65° C. In one embodiment, the mixture is maintained at about 50° C. to about 60° C. The reactor bed is maintained at a temperature at which the aromatic hydroxy compound reacts with the ketone to provide a 1,1,1-tris(4-hydroxyphenyl)compound product. The temperature may be maintained using oil circulators. The temperature of the oil may be measured using thermocouples inserted in the oil circulator. Typically, the temperature is maintained at about 30° C. to about 120° C. and more specifically at about 40° C. to about 100° C. In one embodiment, the temperature in the bed is maintained at about 55° C. to about 75° C.

The weighted hourly space velocity (hereinafter referred to as WHSV) at which the mixture of the aromatic hydroxy compound, the ketone and the optional co-catalyst are fed in a continuous reaction mode varies from about 0.2 to about 5 and more specifically from about 0.3 to about 3. In one embodiment, the WHSV of the mixture of the aromatic hydroxy compound, the ketone and the optional co-catalyst varies from about 0.5 to about 1.

Optionally, the reaction may be carried out in an inert atmosphere such as in the presence of nitrogen, helium or argon.

Any acidic ion exchange resin is used in the reaction of the aromatic hydroxy compound and the ketone. As used herein the term "acidic ion exchange resin" refers to a cation exchange resin in the hydrogen form, wherein the hydrogen ions are bound to the active sites. The hydrogen ions can be removed either by dissociation in solution or by replacement with other positive ions. The active sites of the resin have different attractive strengths for different ions, and this selective attraction serves as a means for ion exchange. Non-limiting examples of suitable acidic ion exchange resins include the series of sulfonated divinylbenzene-crosslinked styrene copolymers, such as for example, copolymers crosslinked with about 1 to about 20 weight percent of divinylbenzene relative to the overall weight of the acidic ion-exchange resin. More specifically, suitable catalysts include acidic ion exchange resins crosslinked with lower than or equal to about 8 weight percent of divinylbenzene relative to the overall weight of the acidic ion exchange resin catalyst. In one embodiment, suitable catalysts include acidic ion exchange resins crosslinked with greater than or equal to about 2 weight percent of divinylbenzene relative to the overall weight of the acidic ion exchange resin catalyst.

Exemplary ion exchange resins include, but are not limited to, Diaion® SK104, Diaion® SK1B, Diaion® PK208, Diaion® PK212 and Diaion® PK216 (manufactured by Mitsubishi Chemical Industries, Limited), A-121, A-232, A-131, and A-15 (manufactured by Rohm & Haas), T-38, T-66, T-63 and T-3825 (manufactured by Thermax), Lewatit K1131 and Lewatit K1221 (manufactured by Bayer), Dowex® 50W2X, Dowex® 50W4X and Dowex® 50W8X resins (manufactured by Dow Chemical), Indion 180 and Indion 225 (manufactured by Ion Exchange India Limited), and Purolite CT-222 and Purolite CT-122 (manufactured by Purolite).

The optional co-catalyst is generally selected from the group consisting of a mercaptan compound, a hydroxy benzene compound, and a hydroxy naphthalene compound.

Typically, the mercaptan compound comprises a compound of Formula (IV):

$$[B_2\text{\textemdash}]_m[A][B_1],\qquad\text{(IV)}$$

wherein A is a monovalent or divalent aliphatic radical, aromatic radical or cycloaliphatic radical; $B_2$ is selected from the group consisting of hydrogen, a hydroxyl, —S—H, —S—$R^3$, —COO$R^4$ and SO$_3R^4$; and $B_1$ is selected from the group consisting of —S—H, —S—$R^3$, —SCOO$R^4$ and SCO$R^4$, wherein $R^3$ is a tertiary alkyl group having 4 to 25 carbon atoms and $R^4$ is selected from the group consisting of hydrogen, an aliphatic group having 1 to 12 carbon atoms, a cycloaliphatic group having 3 to 12 carbon atoms and an aromatic group having 3 to 12 carbon atoms; and m is an integer having a value of 0 or 1.

Optionally, the mercaptan co-catalyst can be employed in salt form. If the co-catalyst employed is in the salt form, the salt gets converted to the free acid of the co-catalyst in situ when it comes in contact with the ion exchange resin catalyst. For example, a sodium salt of 3-mercaptopropane sulfonic acid can be converted to 3-mercaptopropane sulfonic acid upon contact with the acid catalyst.

Non-limiting examples of suitable mercaptan co-catalysts include 3-mercaptopropionic acid (hereinafter called 3-MPA), a substituted or an unsubstituted benzyl mercaptan, 3-mercapto-1-propanol, ethyl 3-mercaptopropionate, 1,4-bis (mercaptomethyl)benzene, 2-mercaptoethane-sulfonic acid, 3-mercaptopropanesulfonic acid, 4-mercaptobutanesulfonic acid, 4-mercaptopentane-sulfonic acid, 3-mercapto-2,2-dimethylpropanesulfonic acid, 2,3-dimercaptopropane-sulfonic acid, mercaptopropane-2,3-disulfonic acid, 2-benzyl-4-mercaptobutanesulfonic acid, 5-mercaptopentane-sulfonic acid, methanethiol, ethanethiol, isopropanethiol, butanethiol and mixtures of the foregoing mercaptan co-catalysts. In one embodiment, 3-mercaptopropane sulfonic acid can be utilized because of its commercial availability and low cost, among others.

Non-limiting examples of suitable hydroxybenzene and hydroxy naphthalene compounds include resorcinol, catechol, hydroquinone, and the mono- and di-methyl and mono- and di-ethyl ethers thereof, para-ethyl phenol, ortho-cresol, para-cresol, phloroglucinol, alpha-naphthol, 5-methyl-alpha-naphthol, 6-isobutyl-alpha-naphthol, 1,4-dihydroxynaphthalene, 6-hexyl-1,4-dihydroxy naphthalene and 6-methyl-4-methoxy-alpha-naphthalene.

Typically, when the co-catalyst is employed in the reaction, the amount used varies from about 0.01 weight percent to about 10 weight percent based on total weight of the reaction mixture. In other embodiments, the quantity of co-catalyst employed is 0.05 weight percent to 5 weight percent based on total weight of the reaction mixture. In still other embodiments, the quantity of co-catalyst employed is 0.75 weight percent to 3 weight percent based on total weight of the reaction mixture.

The reaction mixture so-obtained may then be contacted with a solvent to precipitate a solid material, e.g., the 1,1,1-tris(4-hydroxyphenyl)compound. The solvent used for the precipitation can be, but is not limited to, chlorinated solvents, toluene, xylene or mixtures of the foregoing solvents thereof. Non-limiting examples of suitable chlorinated solvents include methylene chloride, ethylene dichloride, dichlorobenzene and chlorobenzene. In one embodiment, the solvent used is ethylene dichloride. Generally, the amount of solvent used comprises a volume ratio to the reaction mixture of at least 2:1, more specifically the volume ratio is 2.5:1, and most specifically the volume ratio is 3:1. More solvent may be used, but this may lead to a decrease in the yields of 1,1,1-tris(4-hydroxyphenyl)compound. The pale yellowish brown solid material that precipitates contains at least 90% by weight of the particular 1,1,1-tris (4-hydroxyphenyl)compound.

The solid material comprising 1,1,1-tris (4-hydroxyphenyl)compound so-obtained may then be subjected to different purification techniques. Typically, when THPE is prepared using the above disclosed process, the solid material comprises THPE, bisphenol-A (hereinafter referred to as BPA) and phenol. In one embodiment the solid material may subsequently be contacted with a methanol-water mixture containing at least 20% methanol by volume for 0.5 to 2 hours. In one embodiment, the proportion of methanol in the methanol-water mixture is of the order of 20-40% by volume. The solid material may then be further refluxed in a mixture comprising an alcohol containing a decolorizing agent. Suitable decolorizing agents include, but are not intended to be limited to, alkali metal borohydrides, alkali metal dithionites, activated charcoal, combinations comprising at least one of the foregoing decolorizers, and the like. Suitable alcohols comprise straight chain or branched or cyclic aliphatic alcohols containing from 1 to 8 carbon atoms. Non-limiting examples of suitable aliphatic alcohols include methanol, ethanol, iso-propanol, iso-butanol, n-butanol, tertiary-butanol, n-pentanol, iso-pentanol, mixtures of at least one of the foregoing aliphatic alcohols, and the like. The mixture may optionally be treated with activated charcoal to achieve further decolorization if desired. The mixture can then be treated with water, optionally containing the decolorizing agent, to precipitate a visually colorless 1,1,1-tris(4-hydroxyphenyl)alkane, for example.

In one other embodiment, the solid material comprising 1,1,1-tris (4-hydroxyphenyl)compound may be purified by employing an adduct crystallization technique. In this purification method, for example, when THPE is being purified, THPE is mixed with BPA or phenol or a mixture of BPA and phenol and this mixture is heated to a temperature such that a homogenous solution is obtained. Typically, the temperature required to achieve the homogenous solution varies from about 50° C. to about 180° C., and more specifically, from about 100° C. to about 140° C. In one embodiment, the temperature varies from about 120° C. to about 130° C. The time taken to obtain the homogenous solutions varies from about 10 minutes to about 3 hrs and more specifically from about 0.5 hours to about 2 hours. In one embodiment the time is 1 hr. The system is maintained in the homogenous molten state for another 0.5 hours to about 3 hours to ensure the formation of a uniform homogeneous mixture before being cooled down. Subsequently, the temperature is decreased at a rate of about 1° C. per minute to about 10° C. per minute, and more specifically, at 1 ° C. per minute. Solid THPE precipitates out at about 50° C. to about 150° C., and more specifically, at about 100° C. to about 140° C. In one embodiment, the solid precipitates at about 120° C. to about 130° C. The system is then left untouched for about 1 hour to about 15 hours to obtain complete precipitation of the solids. The solids are then filtered and dried. The solids so obtained are analyzed using high performance liquid chromatography (hereinafter referred to as HPLC) technique. In one embodiment, the reaction mixture before being contacted with the solvent to precipitate the 1,1,1-tris (4-hydroxyphenyl)compound can be directly subjected to the adduct formation process described above.

For example, when THPE is purified using the adduct purification method, the THPE-BPA-phenol or THPE-BPA or THPE-phenol adduct so formed may then be subjected to a desorption step to obtain about 95% pure THPE. The adduct is first washed with a solvent and then subjected to a methanol-water crystallization step. The solvent used for desorption includes, but is not limited to, chlorinated solvents, toluene, xylene or mixtures of the foregoing solvents thereof. Non-limiting examples of suitable chlorinated solvents include methylene chloride, ethylene dichloride, dichlorobenzene and chlorobenzene. In one embodiment, the solvent used is toluene. Generally, the amount of solvent used comprises a volume ratio to the reaction mixture of at least 2:1, more specifically the volume ratio is 2.5:1, and most specifically the volume ratio is 3:1. More solvent may be used, but this may lead to a decrease in the yields of 1,1,1-tris(4-hydroxyphenyl)compound. For the methanol-water crystallization step, the adduct may be contacted with a methanol-water mixture containing at least 20% methanol by volume for 0.5 to 2 hours. In one embodiment, the proportion of methanol in the methanol-water mixture is on the order of 20-40% by volume. In one embodiment the desorption may also be carried out by subjecting the THPE adduct melt to distillation to strip off phenol.

In one embodiment, the ion exchange resin catalyst may be reused for subsequent reactions. For example, in a batch mode reaction, the catalyst may be filtered off and reused in the next batch reaction. In the continuous mode, the fixed bed reactor may be subjected to multiple passes of the reactants for a number of hours. Unreacted phenol and ketone may be recovered and reused in the process. Both the above described purification techniques result in effluent comprising 1,1,1-tris(4-hydroxyphenyl)compound. This effluent may also be recycled in the reaction.

As previously discussed, the 1,1,1-tris(4-hydroxyphenyl) compounds obtained herein can be used as branching agents such as may be desired for producing —branched polycarbonates. For example, THPE can be added to the reactants used during polymerization. The desired rheological effects of branching provide higher viscosities and higher melt strengths relative to an otherwise similar resin prepared without using THPE. Branched polycarbonates derived from 1,1,1-tris(4-hydroxyphenyl)compound are suitable for use as films or sheets. The branched polycarbonates can also be blow molded to prepare structured containers.

A number of polymerization methods can be used for producing the branched polycarbonates, comprising the 1,1,1-tris(4-hydroxyphenyl)compounds. Suitable methods for fabricating these polycarbonates, for example, include a melt transesterification polymerization method and an interfacial polymerization method.

The melt transesterification polymerization method is generally carried out by combining a catalyst (e.g., quaternary phosphonium salts or sodium hydroxide or tetraalkylammonium salts) and a reactant composition to form a reaction mixture. Next the reaction mixture is mixed under sufficient pressure and temperature conditions for a time period effective to produce a branched polycarbonate. The resultant product mixture generally comprises a carbonic acid diester of the formula $(ZO)_2C=O$, wherein each Z is independently an unsubstituted or a substituted alkyl radical, or an unsubstituted or a substituted aryl radical and the 1,1,1-tris(4-hydroxyphenyl)compound.

In the interfacial polymerization method, 1,1,1-tris(4-hydroxyphenyl)compound, one or more co-monomers, and phosgene are reacted in the presence of an acid acceptor and an aqueous base to produce a polycarbonate. Tertiary amines, such as for example, trialkylamines are preferably used as acid acceptors. An exemplary trialkylamine is triethylamine. Suitable aqueous bases include, for example, the alkali metal hydroxides, such as sodium hydroxide.

The following examples fall within the scope of, and serve to exemplify, the more generally described methods set forth above. The examples are presented for illustrative purposes only, and are not intended to limit the scope of the disclosure.

In the following examples, a high performance liquid chromatography (HPLC) technique was used to quantify the conversion of the aromatic hydroxy compound of Formula (II) and the ketone of Formula (III) to the particular 1,1,1-tris(4-hydroxyphenyl)alkane. The HPLC was initially calibrated using standard samples of the aromatic hydroxy compound, the ketone, the 1,1,1-tris(4-hydroxyphenyl)alkane, and the bisphenol. The standard samples were diluted with acetonitrile and injected into a Zorbax XDB, C8 5μ reverse phase column commercially available from Agilent Technologies. The reaction mixture was withdrawn at regular time intervals, diluted with acetonitrile and injected to the HPLC column and compared to the HPLC chromatogram of the standard samples to follow the formation of 1,1,1-tris (4-hydroxyphenyl) alkane in the reaction.

The color value of the 1,1,1-tris(4-hydroxyphenyl)alkanes prepared by following the methods of this disclosure preferably have a percentage transmission at the corresponding wavelengths in nanometers (nm) as indicated in Table 1 below

TABLE 1

| Wavelength in nm | % Transmission not less than |
| --- | --- |
| 440 | 50 |
| 560 | 80 |
| 630 | 80 |

EXAMPLE 1

This example provides the preparation of THPE using 2,4-pentanedione (PD), phenol, 3-mercapto propane sulfonic acid (3-MPSA) in a batch mode.

In a 1 liter 4-necked round bottom flask equipped with a mechanical stirrer, thermometer pocket, and a water-cooled reflux condenser with a calcium chloride guard and an air leak tube was charged phenol (306 grams (g)), IER A-121 (2% crosslink; 23 g) and 3-MPSA sodium salt (6.62 g). The flask was immersed in an oil bath and the oil bath was maintained at 40° C. PD (25 g) was added drop-wise to the reaction mixture over a period of 10 minutes under stirring. The temperature of the oil bath was then raised to 75° C. when the reaction mixture turned red in color due to the dissolution of the 3-MPSA solids. The stirring was continued for about another 22 hours and this resulted in a thick red colored slurry. The slurry was then filtered and the filtrate was poured into a 2 liter conical flask and diluted with 1,150 milliliters (ml) of ethylene dichloride and stirred for about another 3 hours at room temperature (i.e., 25° C.). The precipitated THPE solids were filtered and washed with about 150 ml of ethylene dichloride till a colorless filtrate was obtained. The solids were again washed with about 200 ml of water.

The purification process included stirring the crude reaction product into a methanol-water mixture (40:60 volume by volume, 150 ml) for 0.5 hours. Next the solids were filtered off, dried. The solids so obtained were then dissolved in methanol (62 ml). Sodium borohydride ($NaBH_4$, 50 milligrams (mg)) was added to this mixture, followed by stirring for half an hour, to provide a pale yellow colored solution. To this solution 124 ml. of deionized water containing 50 mg of $NaBH_4$ was added dropwise in about an hour, and the mixture was stirred for another hour. Colorless solids precipitated out, which were filtered and washed with water (150 ml.) and dried. The solids were dried at 60° C. under vacuum to constant weight. The color value of the 1,1,1-tris(4-hydroxyphenyl)ethane prepared above was found to have acceptable percentage transmission (% T) at the corresponding wavelengths as indicated in Table 2 below.

TABLE 2

| Wavelength (nanometers) | % T (Reference Value) | % T for THPE prepared in example 1 |
| --- | --- | --- |
| 440 | 50 | 74 |
| 560 | 80 | 89 |
| 630 | 80 | 93 |

The color values were analyzed spectrophotometrically by weighing 2.5 grams of the particular 1,1,1-tris(4-hydroxyphenyl)alkane in a 30 milliliters vial and dissolving the sample in 5 grams of methanol. The percentage transmission was then measured using this solution in a UV-visible spectrophotometer in the range of 300 nm to 750 nm.

EXAMPLES 2-7

These examples provide a method for the preparation of THPE as generally outlined in Example 1. Examples 2-5 employed 3-MPSA as the co-catalyst whereas Examples 6-7 utilized 3-MPA. The reaction contents, time, and yields are included in Table 3 below. All the reactions were carried out at a temperature of about 65° C. The weight percent of the co-catalyst and catalyst used is based on the total weight of the reaction mixture, i.e., total weight of phenol and PD.

TABLE 3

| Ex. | PD (g) | Phenol (g) | Co-catalyst (g) | IER Resin A-121 (g) | Time (hours) | HPLC analysis results THPE yield (%) | BPA yield (%) |
|---|---|---|---|---|---|---|---|
| 2 | 4.1 | 50 | 0.54 3-MPSA | 4.33 | 2 | 7.43 | 2.27 |
|   |     |    |               |      | 4 | 0.53 | 4.27 |
|   |     |    |               |      | 20 | 40.91 | 62.68 |
|   |     |    |               |      | 22 | 46.34 | 67.87 |
|   |     |    |               |      | 24 | 45.66 | 67.15 |
|   |     |    |               |      | 26 | 51.96 | 70.76 |
|   |     |    |               |      | 46 | 57.47 | 71.18 |
|   |     |    |               |      | 48.5 | 57.16 | 71.16 |
| 3 | 4.1 | 50 | 1.08 3-MPSA | 4.89 | 2 | 2.08 | 1.11 |
|   |     |    |             |      | 4 | 0.39 | 2.05 |
|   |     |    |             |      | 20 | 46.24 | 62.67 |
|   |     |    |             |      | 22 | 49.65 | 64.94 |
|   |     |    |             |      | 24 | 48.07 | 66.19 |
|   |     |    |             |      | 26 | 49.30 | 66.32 |
|   |     |    |             |      | 28 | 48.04 | 65.54 |
|   |     |    |             |      | 48.5 | 54.65 | 67.73 |
| 4 | 4.1 | 50 | 1.62 3-MPSA | 4.89 | 2 | 4.19 | 2.09 |
|   |     |    |             |      | 4 | 14.84 | 9.88 |
|   |     |    |             |      | 20 | 46.22 | 66.37 |
|   |     |    |             |      | 26 | 44.90 | 64.92 |
|   |     |    |             |      | 28.5 | 49.36 | 66.97 |
|   |     |    |             |      | 28.5 | 49.85 | 67.15 |
| 5 | 2.7 | 50 | 0.54 3-MPSA | 3.20 | 20 | 57.60 | 70.49 |
|   |     |    |             |      | 22 | 56.55 | 71.09 |
|   |     |    |             |      | 26 | 60.79 | 74.41 |
|   |     |    |             |      | 44 | 58.36 | 74.98 |
|   |     |    |             |      | 46 | 58.79 | 72.86 |
|   |     |    |             |      | 46 | 59.00 | 73.06 |
| 6 | 2.5 | 47 | 0.79 3-MPA | 4.95 | 24 | 49.05 | 78.15 |
| 7 | 2.5 | 47 | 0.79 3-MPA | 9.90 | 18 | 45.94 | 80.92 |

EXAMPLES 8-10

These examples provide a method for preparing THPE in the absence of a co-catalyst. The reaction was carried out in a similar manner as described in Example 1 above using A-121 2% cross linked ion exchange resin at a temperature of 75° C. in the absence of a co-catalyst. The reaction contents, reaction parameters, and HPLC analysis results are included in Table 4 below.

TABLE 4

| Example | Catalyst (A-121) (g) | Phenol (g) | PD (g) | Time (hours) | HPLC Analysis THPE Yield % | BPA Yield % |
|---|---|---|---|---|---|---|
| 8 | 2.48 | 47 | 2.503 | 46 | 47.80 | 40.69 |
| 9 | 4.95 | 47 | 2.503 | 24 | 48.82 | 60.21 |
| 10 | 7.43 | 47 | 2.503 | 24 | 42.59 | 72.82 |

EXAMPLE 11

In this example, THPE was purified by forming the adduct. In a 500 ml round bottom flask, THPE (15.37 g), BPA (11.4 g) and phenol (37.64 g) (THPE:BPA:phenol::1:1:8) were taken and heated to about 150° C. in an hour to obtain a homogenous solution. The heating was continued for another 1 hour and then the temperature was decreased at a rate of about 1° C. per minute, when the solids precipitated out at about 126° C. The mixture was then allowed to stand for another 20 minutes and then filtered. The product obtained was analyzed using HPLC and indicated 60.61 weight percent (wt. %) THPE, 10.71 wt. % BPA and 28.66 wt. % phenol.

EXAMPLES 12-20

In these examples, THPE adduct was prepared using the method described in Example 6 above. The reaction contents and reaction parameters are tabulated in Table 5 and the results are tabulated in Table 6 below. Table 6 includes the HPLC analysis results of the amount of THPE, BPA and phenol in the adduct and in the effluent.

TABLE 5

| | Reaction Contents | | | Temperature in ° C. | | Wt. of THPE |
|---|---|---|---|---|---|---|
| Example | BPA in g | THPE in g | Phenol in g | Homogenous Solution | Adduct Formation | taken (g) |
| 12 | 11.4 | 15.4 | 28.2 | 160 | 135–139 | 15.3 |
| 13 | 11.4 | 15.4 | 37.6 | 150 | 126–128 | 15.3 |
| 14 | 11.4 | 15.3 | 56.5 | 135 | 103 | 15.3 |
| 15 | 13.7 | 18.4 | 112.9 | 130 | 55 | 18.4 |
| 16 | — | 15.4 | 28.2 | 165 | 143–145 | 15.4 |
| 17 | — | 15.4 | 37.6 | 150 | 133 | 15.4 |
| 18 | — | 61.2 | 150.4 | 150 | 135 | 61.2 |

TABLE 5-continued

| Example | Reaction Contents | | | Temperature in ° C. | | Wt. of THPE taken (g) |
|---|---|---|---|---|---|---|
| | BPA in g | THPE in g | Phenol in g | Homogenous Solution | Adduct Formation | |
| 19 | — | 7.65 | 28.2 | 135 | 117 | 7.6 |
| 20 | — | 7.65 | 37.6 | 130 | 95–98 | 7.6 |

TABLE 6

| | Wt. of | HPLC Analysis Adduct (Solid) | | | HPLC Analysis (Effluent filtrate) | | |
|---|---|---|---|---|---|---|---|
| Example | Adduct (g) | THPE wt % | BPA wt % | PHENOL wt % | THPE wt. % | BPA wt. % | PHENOL wt. % |
| 12 | 8.70 | 60.59 | 15.99 | 23.42 | 23.42 | 21.86 | 54.72 |
| 13 | 12.22 | 60.61 | 10.72 | 28.67 | 16.73 | 21.54 | 61.72 |
| 14 | 10.60 | 54.47 | 11.06 | 34.48 | 12.56 | 16.09 | 71.35 |
| 15 | 6.52 | 48.83 | 7.52 | 43.66 | 12.03 | 10.66 | 77.31 |
| 16 | 6.09 | 83.20 | 0.50 | 16.31 | 26.81 | 0.25 | 72.94 |
| 17 | 9.70 | 85.46 | 0.00 | 14.54 | 20.21 | 0.34 | 79.45 |
| 18 | 21.83 | 76.62 | 0.38 | 23.00 | 25.15 | 0.29 | 74.56 |
| 19 | 2.45 | 87.97 | 0.45 | 11.58 | 19.61 | 0.29 | 80.09 |
| 20 | 2.20 | 77.82 | 0.35 | 21.83 | 11.93 | 0.26 | 87.81 |

EXAMPLE 21

In this example, THPE was prepared as per example 1 given above, and then the catalyst was recycled 10 times. The reactants phenol, PD and 3-MPA were taken along with A-121 2% CL IER catalyst and heated at 75° C. for 24 hours. This mixture was filtered off to obtain the catalyst and to the filtrate was added 3:1 volume by volume ethylene dichloride based on the total volume of the reaction mixture. The catalyst was then again washed with about 50 ml ethylene dichloride and reused in the next batch. The catalyst was recovered in a similar manner as described above and reused for 9 subsequent batches using the quantity of phenol, PD and 3-MPA provided in Table 7 below. Table 7 also indicates the wt. % of the THPE and BPA as obtained by HPLC analysis of the reaction mixture.

TABLE 7

| Example | Phenol in g | PD in g | 3-MPA in g | IER Catalyst in g | Time in hours | HPLC analysis THPE Yield % | BPA yield % |
|---|---|---|---|---|---|---|---|
| 21 | 282 | 15.023 | 4.77 | 32.1 | 24 | NA | NA |
| 21a | 282 | 15.02 | 4.77 | Recycled from 21 | 24 | 33.41 | 54.25 |
| 21b | 282 | 15.02 | 4.77 | Recycled from 21a | 24 | NA | NA |
| 21c | 282 | 15.02 | 4.77 | Recycled from 21b | 24 | 41.38 | 62.31 |
| 21d | 282 | 15.02 | 4.77 | Recycled from 21c | 24 | NA | NA |
| 21e | 282 | 15.02 | 4.77 | Recycled from 21d | 24 | NA | NA |
| 21f | 282 | 15.02 | 4.77 | Recycled from 21e | 24 | NA | NA |
| 21g | 282 | 15.02 | 4.77 | Recycled from 21f | 24 | 24.31 | 30.09 |
| 21h | 282 | 15.02 | 4.77 | Recycled from 21g | 24 | 24.84 | 28.95 |
| 21i | 282 | 15.02 | 4.77 | Recycled from 21h | 24 | 24.47 | 26.78 |

NA → data not available.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. The disclosure is further illustrated by the following non-limiting examples.

The invention claimed is:

1. A method comprising;

reacting a mixture of an aromatic hydroxy compound and a ketone in the presence of at least one ion exchange resin catalyst to produce a 1,1,1-tris(4-hydroxyphenyl) compound of formula:

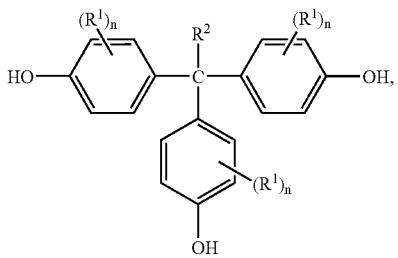

wherein the aromatic hydroxy compound has a formula of,

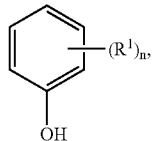

wherein the ketone has a formula of,

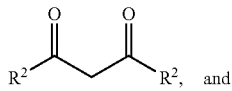

wherein $R^1$ and $R^2$ are independently at each occurrence selected from the group consisting of an aliphatic radical, a cycloaliphatic radical and an aromatic radical; "n" is an integer of value 0 to 3.

2. The method of claim 1, wherein the mixture is reacted in the presence of the at least one ion exchange resin catalyst and a mercaptan co-catalyst.

3. The method of claim 1, wherein the 1,1,1-tris(4-hydroxyphenyl)compound is 1,1,1-tris (4-hydroxyphenyl) ethane.

4. The method of claim 1, wherein the aromatic hydroxy compound is phenol.

5. The method of claim 1, wherein the ketone is 2,4, pentanedione.

6. The method of claim 1, wherein the aromatic hydroxy compound and the ketone are at a molar ratio of 3-30:1.

7. The method of claim 1, wherein the aromatic hydroxy compound and the ketone are at a molar ratio of 8-15:1.

8. The method of claim 1, wherein reacting the mixture is in a batch mode.

9. The method of claim 8, wherein the ion exchange resin catalyst is present at from 2 to 20 weight percent based on a weight of the aromatic hydroxy compound.

10. The method of claim 1, wherein reacting the mixture is in a continuous mode.

11. The method of claim 10, wherein the mixture of the aromatic hydroxy compound and the ketone is at a weighted hourly space velocity of about 0.2 to about 4.

12. The method of claim 2, wherein the mercaptan co-catalyst has a formula:

$$[B_2\!-\!\!+\!\!_m\!\!+\!\!A\!\!+\!\!+\!B_1],$$

wherein A is an aliphatic radical having 1 to 12 carbon atoms, a cycloaliphatic radical having 3 to 12 carbon atoms or an aromatic radical having 1 to 12 carbon atoms, $B_2$ is selected from the group consisting of a hydrogen, a hydroxyl, —S—H, —S—$R^3$, —COOR$^4$ and SO$_3$R$^4$, $B_1$ is selected from the group consisting of —S—H, —S—$R^3$, —SCOOR$^4$ and SCOR$^4$, wherein $R^3$ is a tertiary alkyl group having 4 to 25 carbon atoms and $R^4$ is selected from the group consisting of a hydrogen and an aliphatic radical having 1 to 12 carbon atoms, a cycloaliphatic radical having 3 to 12 carbon atoms, an aromatic radical having 1 to 12 carbon atoms, and m is an integer having a value of 0 or 1.

13. The method of claim 1, wherein the mercaptan co-catalyst is 3-mercaptopropanesulfonic acid.

14. The method of claim 1, wherein the mercaptan co-catalyst is 0.01 weight percent to 5 weight percent based on a total weight of the mixture.

15. The method of claim 1, wherein reacting the mixture comprises heating the mixture to a temperature of 30° C. to 100° C.

16. The method of claim 1, further comprising reacting the 1,1,1-tris(4-hydroxyphenyl)compound with one or more co-monomers to form a branched polymer.

17. The method of claim 1, further comprising purifying the 1,1,1-tris(4-hydroxyphenyl)compound by forming an adduct.

18. A method for producing 1,1,1-tris(4-hydroxyphenyl) ethane, comprising:
reacting a mixture of phenol and 2,4-pentanedione in the presence of at least one ion exchange resin catalyst and optionally a mercaptan co-catalyst to form the 1,1,1-tris(4-hydroxyphenyl)ethane.

19. The method of claim 18, further comprising purifying 1,1,1-tris(4-hydroxyphenyl)ethane by forming an adduct with bisphenol-A, phenol or a mixture of the bisphenol-A and the phenol.

* * * * *